US00PP11741P2

(12) United States Plant Patent
Pounders, Jr.

(10) Patent No.: US PP11,741 P2
(45) Date of Patent: Jan. 16, 2001

(54) ILEX HYBRID VARIETY NAMED 'HUO YEN'

(76) Inventor: Cecil T. Pounders, Jr., 3140 Old Moulton Rd., Decatur, AL (US) 35603

( * ) Notice: Under 35 U.S.C. 154(b), the term of this patent shall be extended for 0 days.

(21) Appl. No.: 09/198,304

(22) Filed: Nov. 23, 1998

(51) Int. Cl.[7] ..... A01H 5/00
(52) U.S. Cl. ..... Plt./247
(58) Field of Search ..... Plt./247, 226

*Primary Examiner*—Howard J. Locker

(57) ABSTRACT

Huo Yen is a unique new evergreen holly which combines desirable landscape and production traits from two species, *Ilex opaca* and *Ilex cassine*, in a manner which particularly distinguished it from all other forms of Ilex. Plants bear copious annual crops of vibrant red berries (mature color) without loss of foliage color, have distinctive lustrous fine textured lanceolate leaves, produce an erect narrow symmetrical pyramidal crown without extensive shearing, and have the environmental tolerances of the *Ilex opaca* parent. Huo Yen is being marketed under the Dixie Flame Holly trademark.

2 Drawing Sheets

SUMMARY OF THE INVENTION

My invention is a novel, unique, and ornamental form of Ilex selected by me from a group of open pollinated seedlings of *Ilex×attenuata* (*I. opaca×I. cassine*).

My breeding objective was to create a durable decorative shrub which combines the fine leaf texture, dense growth habit and abundant fruit production of *I. cassine* with the better leaf color and improved tolerance of cold and moisture stress of *I. opaca*. This invention comprises a novel amalgamation of attributes from the original species that differentiates it from all other forms of Ilex of which I am aware. The new clone has been named the Huo Yen variety.

The variety exhibits the following combination of traits:

(a) bountiful crops of berries maturing to vibrant red in early fall then persisting until spring, (b) evergreen, fine textured leaves which retain lustrous green coloration even when plant is heavily fruited, (c) robust, balanced crown without extensive shearing, (d) erect narrow pyramidal crown with strong apical dominance, (e) fruiting occurs on initial spring growth thus plants can be pruned without disrupting the annual fruiting cycle, (f) tolerates a wide range of environmental conditions and pest equivalent to *I. opaca.*

Huo Yen variety can be incorporated into landscapes much as *Ilex×attenuata* 'Foster 2' which is extensively planted in the southern United States. In a production environment Huo Yen reveals a self-branching growth habit with strong apical dominance that improves uniformity and substantially reduces production cost when compared to Foster holly. Under landscape conditions Huo Yen fruits more abundantly, has better symmetry and finer textured foliage. Xia Xiang (U.S. Plant Pat. No. 10,526), my other recent introduction, differs from Huo Yen in that Xia Xiang leaves are revolute oblanceolate and a lighter shade of green, fruit is less abundant and about half as large, branching is denser with secondary branches becoming pendulous, and the crown is ultimately broader in relation to the height.

My new variety, Huo Yen, has been asexually propagated by cutting at Mobile, Decatur and Loxley, Ala. Propagules demonstrated that the distinctive combination of characteristics has been established and faithfully transmitted to successive generations.

Huo Yen is being marketed under the Dixie Flame Holly trademark.

BRIEF DESCRIPTION OF THE PHOTOGRAPHS

The accompanying photographs show typical specimens of my new variety of Ilex during fall and early winter as depicted in color as true as is reasonably possible to make the same in color photographs of the character. The specimens illustrated were being grown in the ground at Decatur, Ala. and in nursery containers at Mobile, Ala.

DETAILED DESCRIPTION

Figure 1:
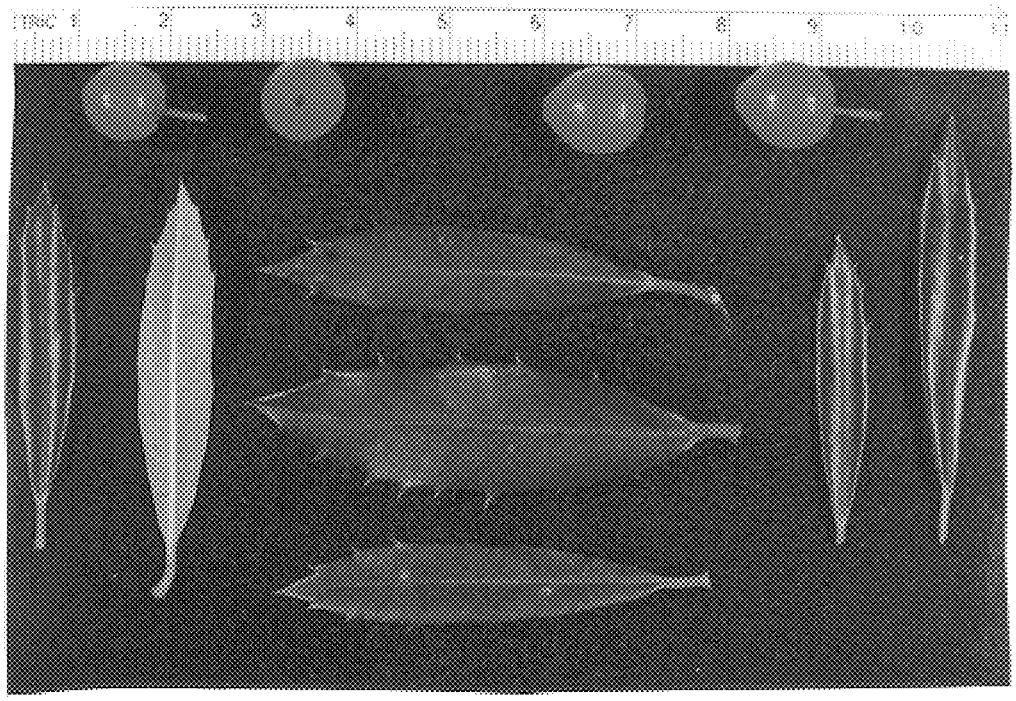
FIG. 1 illustrates fruit and foliage shape, size and color.
Figure 2:
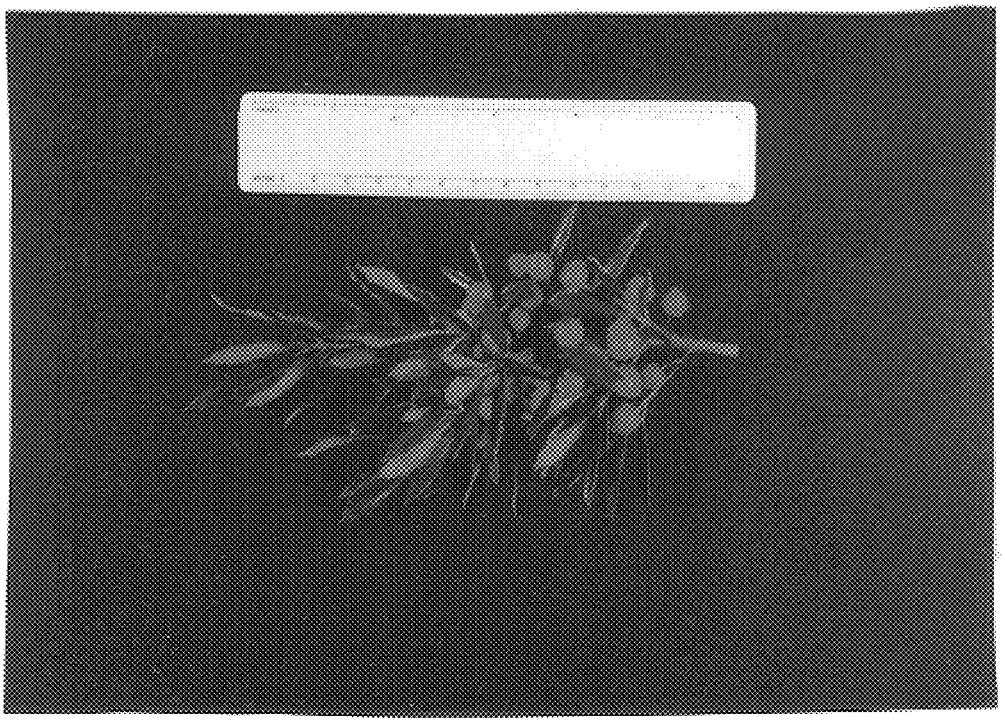
FIG. 2 illustrates fruit set within foliage.
Figure 3:
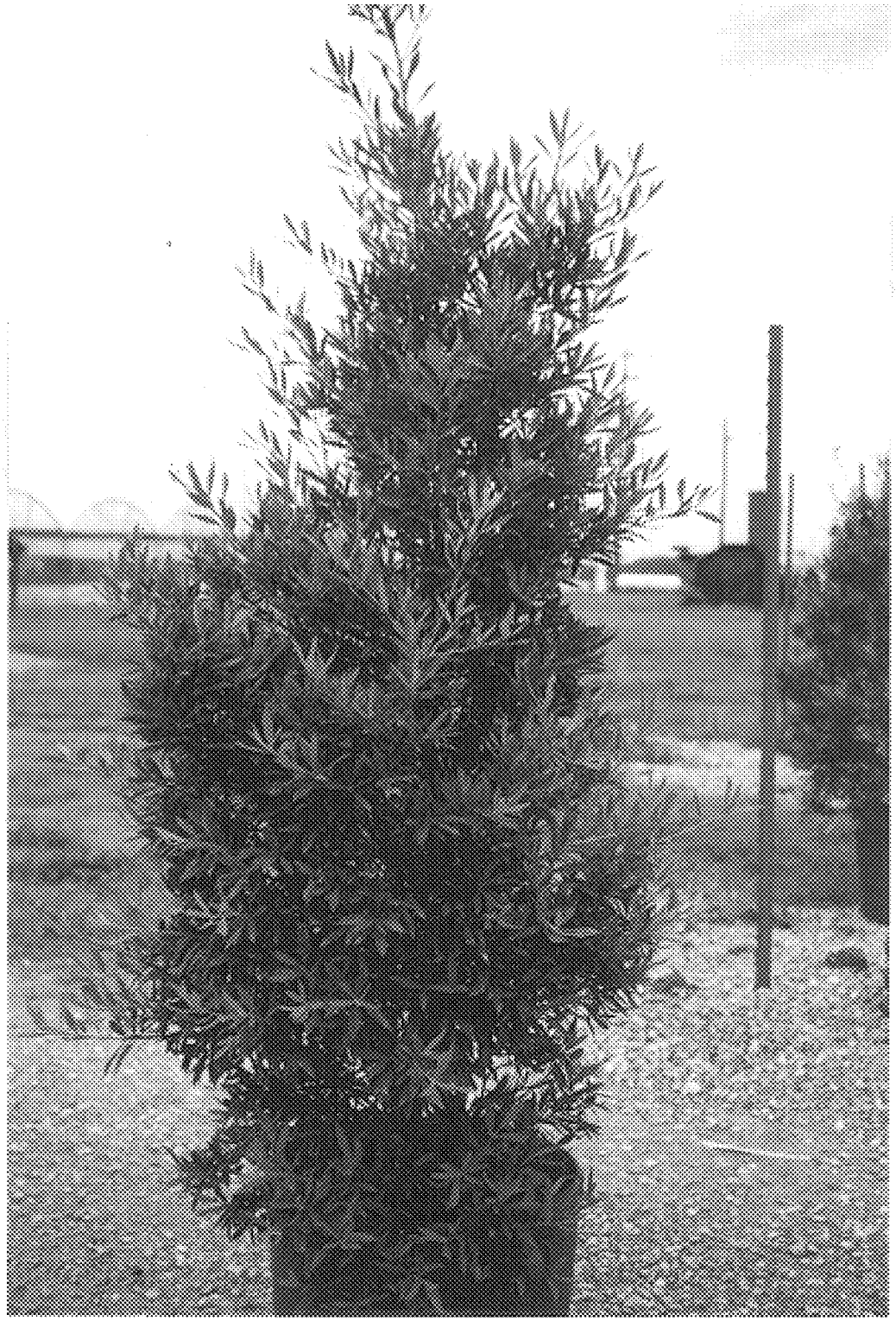
FIG. 3 illustrates a whole plant view of 'Huo Yen'.

The following is a detailed description of my new variety of Ilex made from observation of plants growing in the ground at Decatur, Ala. Color terminology is in accordance with The R.H.S. Colour Chart of The Royal Horticultural Society, London, England.

Class: *Ilex×attenuata.*

Parentage: Originated from open pollinated seed collected from an *Ilex×attenuata* seedling.

Pollinator: Plant may be pollinated by a male plant of either *I. opaca, I. cassine* or *I.×attenuata* with synchronous flowering habit.

Foliage:

*Type.*—Evergreen, semi-glossy, coriaceous. Leaves primarily lanceolate, remotely serrulate with minute spine-tipped teeth, rarely revolute.

*Size.*—Size of leaves is affected by environmental factors such as light intensity and plant nutrient uptake. Leaves are generally in the range of 3–5 cm long and 0.5–1.5 cm wide.

*Petiole.*—Ranges from 2 to 5 mm, initial color Greyed Red Group 179A maturing to Greyed Orange Group 163D.

*Color.*—Upper surfaces of mature leaves are closest to Green Group 147D; lower surface ranges from Yellow Green Group 144A to Yellow Green Group 153D as leaf orientation to sunlight varies. Leaf midvein on upper surface is generally Yellow Green Group 148B.

Stems:

*Color.*—On new growth stems are Greyed Red Group 182B then mature to Greyed Orange Group 163D. Bark on trunks and branched is Grey Group 201D.

Inflorescence and fruit:

*Flowers.*—Small on initial spring growth flush, pistillate, fragrant, usually solitary in leaf axils or at nodes just below leaves; regular calyx, corolla rotate, sepals 4, petals 4; colored Orange White Group 159D, typical of parent species.

*Fruit.*—Drupe containing 4 woody pyrenes; ellipsoid; approximately 1 cm in diameter.

*Fruit color.*—During spring and summer developing fruit is Yellow Green 144B. At maturity fruit is dull to semi-glossy, Red Group 46B.

Plant Growth Characteristics

Plants have an upright pyramidal growth habit with six year individuals growing to approximately 2.5 m in height and 0.5 m in width. Plants establish a dominant central trunk and branching is symmetrical without extensive pruning. Plants bear annual abundant crops of beautiful berries which turn brilliant red at maturity without the loss of foliage color typical of many heavily fruited varieties. Primary branches are silver gray producing an interesting contrast with the red berries and green foliage.

Environmental Tolerance

Testing to date indicates that Huo Yen successfully combines textural qualities of *Ilex cassine* with the environmental adaptions of *Ilex opaca.* This new variety is adapted to the same landscape conditions and climatic range associated with *I. opaca.* No disease or insect damage have been observed. In North Alabama plants have withstood winter temperatures of 10 degrees Fahrenheit and summer droughts that damaged *I. cassine.*

I claim:

1. A new and distinct variety of *Ilex×attenuata* plant, substantially as herein shown and described, characterized particularly as to novelty by the unique combination of:

(a) annual abundant crops of fruit which matures to vibrant red in early fall then persisting until spring, (b) evergreen, fine textured leaves which retain lustrous green coloration even when plant is heavily berried, (c) produces an erect narrow symmetrical pyramidal crown without extensive shearing, and (d) environmental tolerance equivalent to *I. opaca.*

* * * * *